(12) United States Patent
Ritter

(10) Patent No.: US 10,232,100 B2
(45) Date of Patent: Mar. 19, 2019

(54) CONTAINER FOR DIALYSIS CONCENTRATE

(71) Applicant: Ritter GmbH, Schwabmuenchen (DE)

(72) Inventor: Frank Ritter, Eppishausen (DE)

(73) Assignee: Ritter GmbH, Schabmuenchen (DE)

( * ) Notice: Subject to any disclaimer, the term of this patent is extended or adjusted under 35 U.S.C. 154(b) by 0 days.

(21) Appl. No.: 15/573,657

(22) PCT Filed: May 11, 2016

(86) PCT No.: PCT/EP2016/000767
§ 371 (c)(1),
(2) Date: Nov. 13, 2017

(87) PCT Pub. No.: WO2016/184553
PCT Pub. Date: Nov. 24, 2016

(65) Prior Publication Data
US 2018/0117230 A1    May 3, 2018

(30) Foreign Application Priority Data

May 21, 2015  (EP) .................................. 15001528.7

(51) Int. Cl.
*A61M 1/16* (2006.01)
*A61J 1/05* (2006.01)

(52) U.S. Cl.
CPC ........ *A61M 1/1668* (2014.02); *A61M 1/1672* (2014.02); *A61M 2205/128* (2013.01); *A61M 2205/7545* (2013.01)

(58) Field of Classification Search
CPC .. A61M 1/1668; A61J 1/05; A61J 1/14; A61J 1/1412; A61J 1/1443; A61J 1/1468; A61J 1/1475; A61J 1/1481; A61J 1/1487
See application file for complete search history.

(56) References Cited

U.S. PATENT DOCUMENTS

| | | | |
|---|---|---|---|
| 6,247,840 B1 * | 6/2001 | Gaffar ................. | B01F 13/0818 210/321.6 |
| 6,444,174 B1 * | 9/2002 | Lascombes ............ | A61J 3/002 206/219 |
| 2006/0186035 A1 * | 8/2006 | Tryggvason ........ | A61M 1/1656 210/435 |
| 2012/0291891 A1 * | 11/2012 | Ritter .................. | A61M 1/1656 137/544 |

* cited by examiner

*Primary Examiner* — Pranav N Patel
(74) *Attorney, Agent, or Firm* — John H. Thomas, P.C.

(57) ABSTRACT

A dialysis concentrate container for single-use, comprising a container portion (1, 2) which can be filled with dialysis concentrate and a connecting portion (13, 3) connected thereto for connecting the dialysis concentrate container to a dialysis machine, wherein the connecting portion (13, 3) has laterally spaced fluid connection elements (31) for connecting to a fluid outlet and a fluid inlet of the dialysis machine, wherein the container body (1, 2) is formed as a rigid box, wherein the connecting portion (13, 3) is further arranged at the lower end of the container body, wherein the connecting portion (13, 3) is formed by a plate body which can be clamped into a connecting block of the dialysis machine, and on the underside of which the fluid connecting elements (31) are formed, one of which being connected to a fluid inlet of the container body (1) and the other one being connected to a fluid outlet thereof.

11 Claims, 7 Drawing Sheets

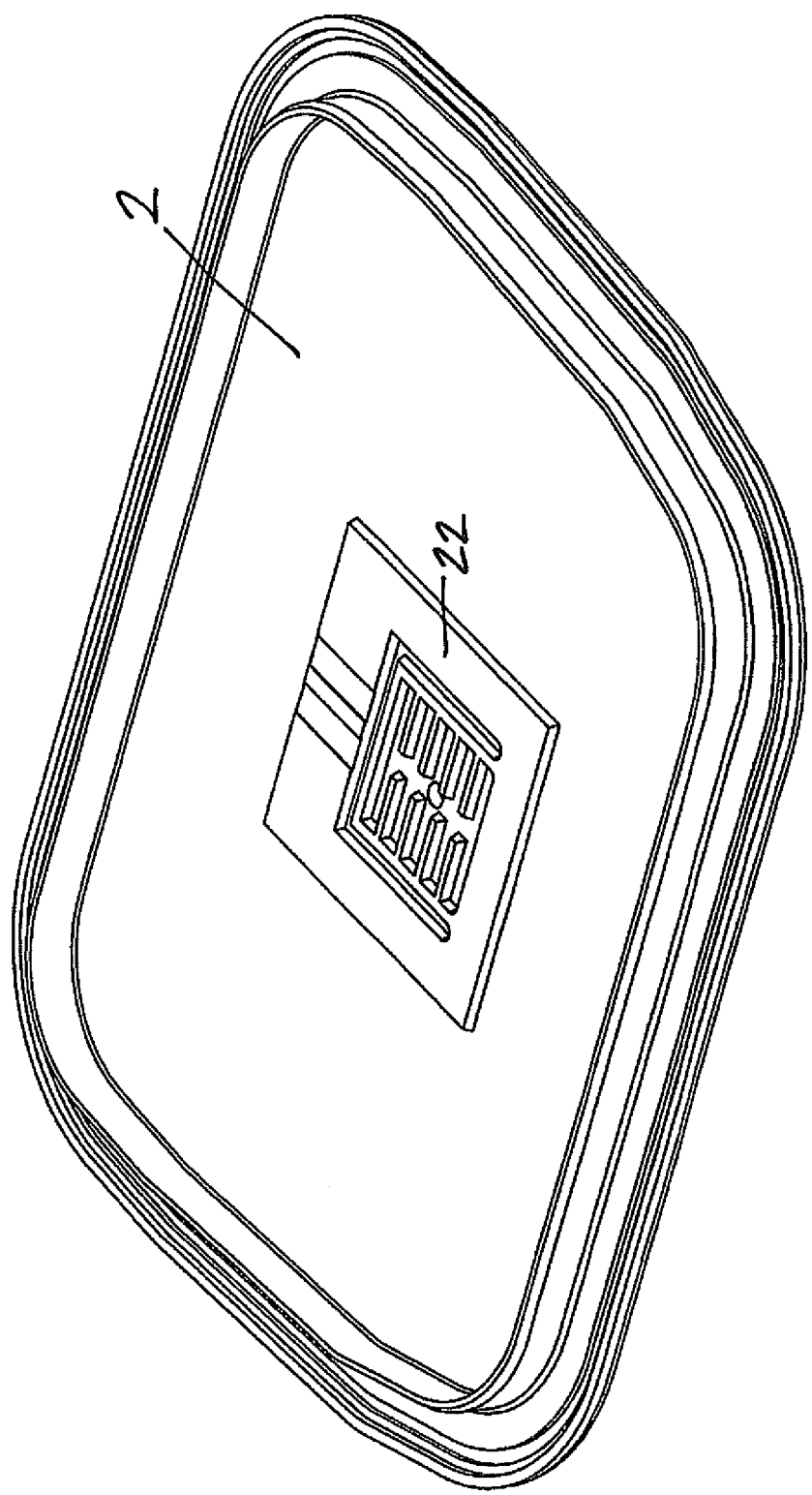

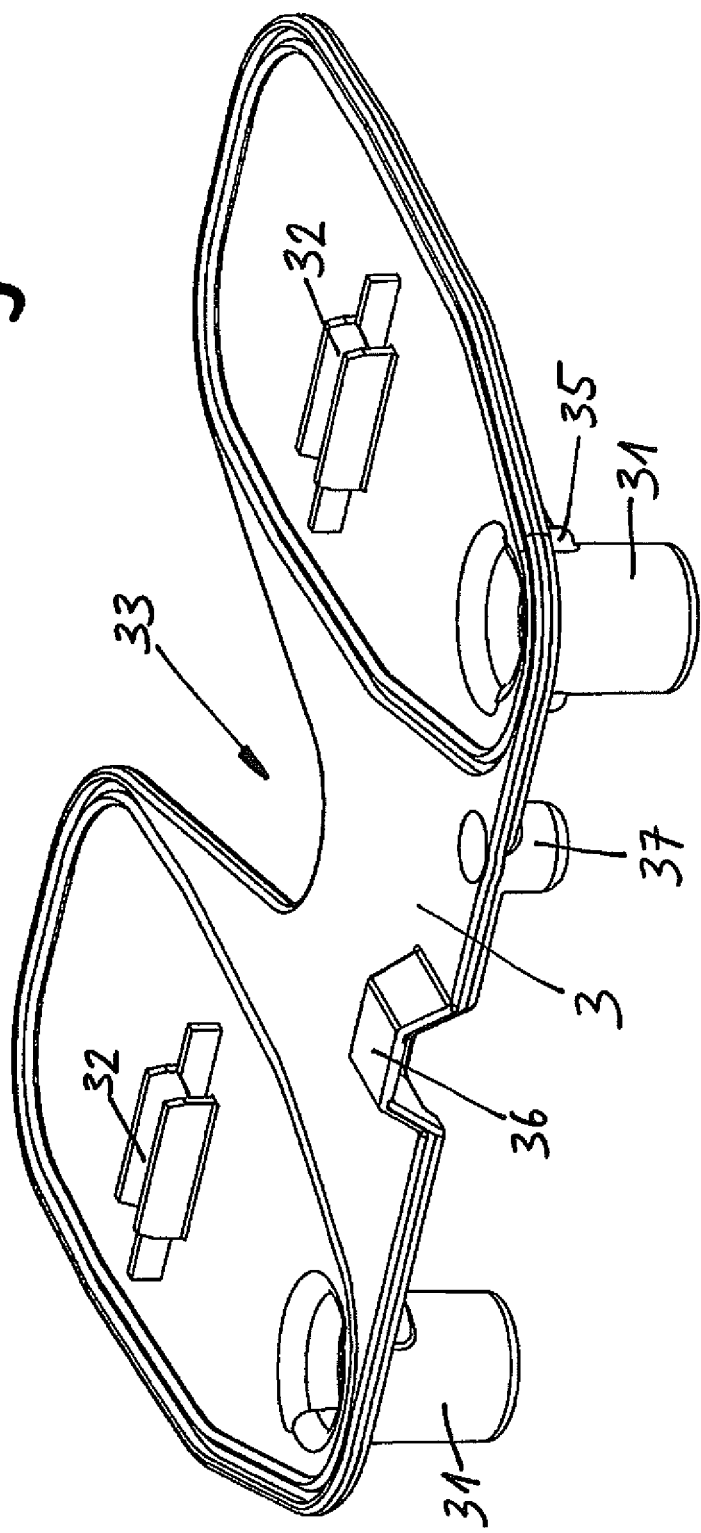

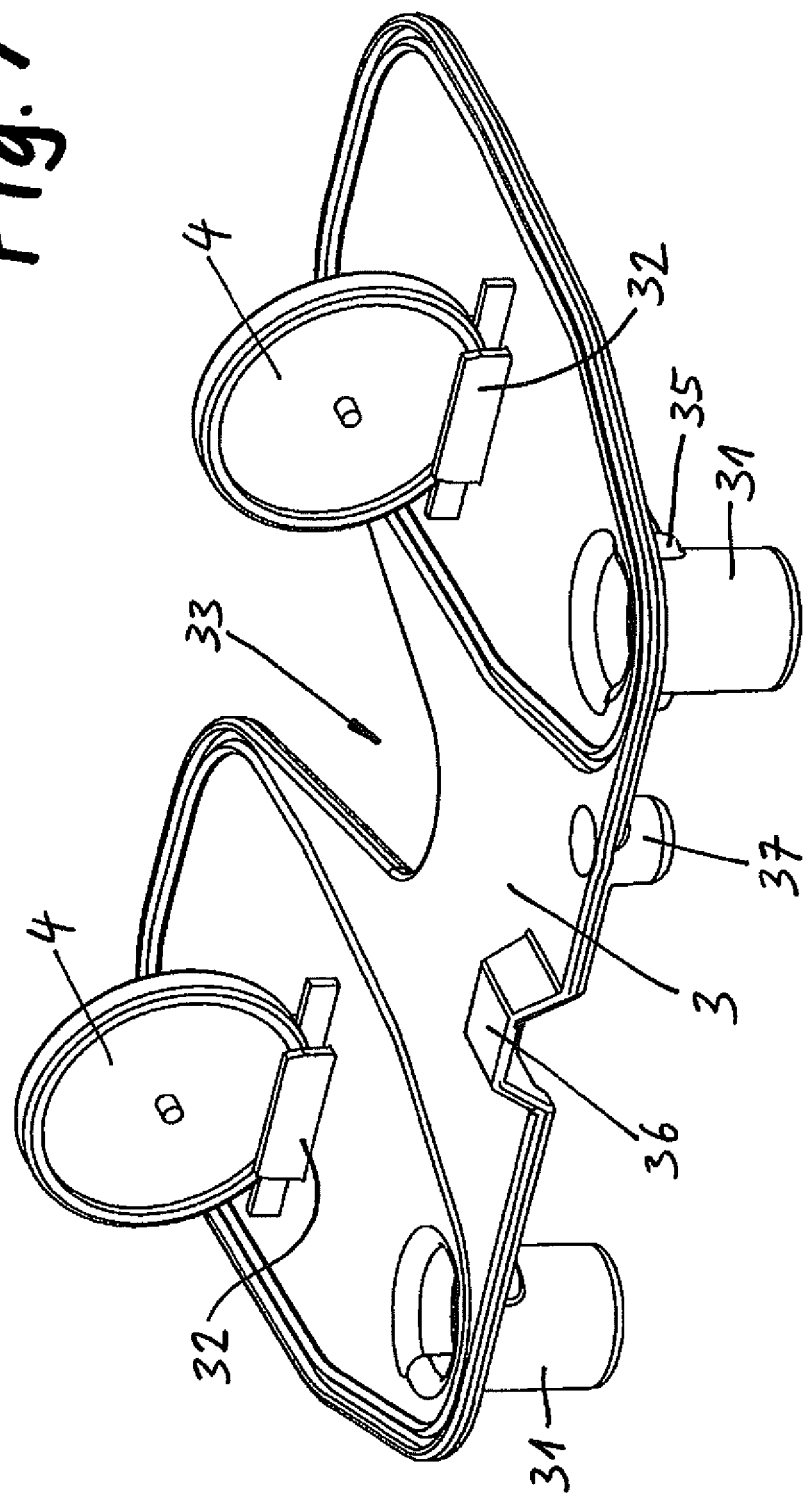

CONTAINER FOR DIALYSIS CONCENTRATE

CROSS-REFERENCE TO RELATED APPLICATIONS

Figure 1:
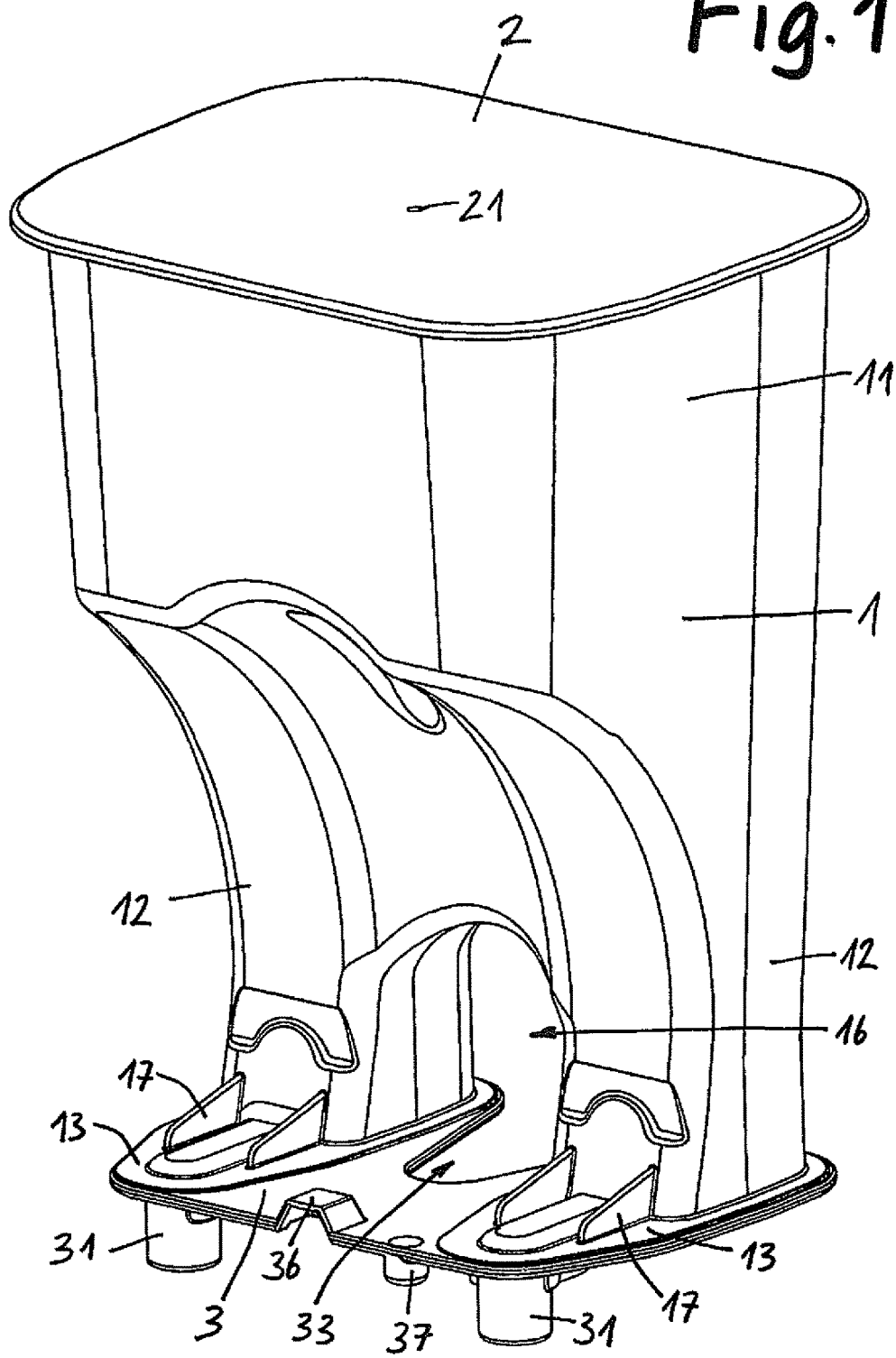

This is a United States Patent Application claiming priority from European Patent Application No. 15001528.7 having a filing date of May 21, 2015, and PCT Patent Application No. PCT/EP 2016/000767, having a filing date of May 11, 2016, the contents of both of which are incorporated herein by reference.

The invention relates to a dialysis concentrate container for single use, filled with a quantity of dialysis concentrate, such as bicarbonate, intended for dialysis treatment, which can be coupled to a connection block of a dialysis machine with two laterally spaced fluid connections.

A dialysis concentrate container of this type is known from EP 1 642 614 B1. The known container consists of a connecting portion provided with inlet and outlet sockets for connecting the container to a connection block of the dialysis machine, and comprising a container portion which connects to the connecting portion at the bottom and is preferably designed as a flexible bag which receives the dialysis concentrate.

This well-known dialysis concentrate container is therefore designed to be coupled to the connection block of the dialysis machine in a hanging arrangement. The hanging arrangement facilitates connecting the container to the dialysis machine, but makes its draining after use more difficult. The design of the container portion of the well-known container as a flexible bag makes it easier to suck off residual liquid because the container can collapse, but makes the production more complex and expensive, since the rigid connecting portion and the flexible container portion have to be made of two different materials and have to be joined together. The fact that the container portion first has to be filled with the dialysis concentrate and then connected with the connecting portion arranged thereabove in the filled state also complicates the manufacturing process.

It is an object of the present invention to create a dialysis concentrate container that overcomes these disadvantages.

According to the invention, this object is achieved by the dialysis concentrate container defined in claim 1. Advantageous embodiments and further developments of the invention are the subject matter of the dependent claims.

The dialysis concentrate container according to the invention is designed as a rigid container made of plastic and is not designed for hanging, but for standing installation on the connection block of the dialysis machine. Its components can all be produced from the same material by injection molding and can be easily connected to each other by welding processes such as ultrasonic welding. More specifically, filling the container with the dialysis concentrate and then closing it is particularly easy because the rigid container can be filled in its standing position and does not require any hanging mechanism; the lid can be a simple lid plate, since all connections are located at the bottom of the container.

The dialysis concentrate container according to the invention consists of a container body with an upper filling opening closed by means of a lid to be connected thereto, and a bottom lid having a connection plate with fluid connection sockets in the lower end region of the container body for connection to the mounting block of the dialysis machine.

Figure 2:
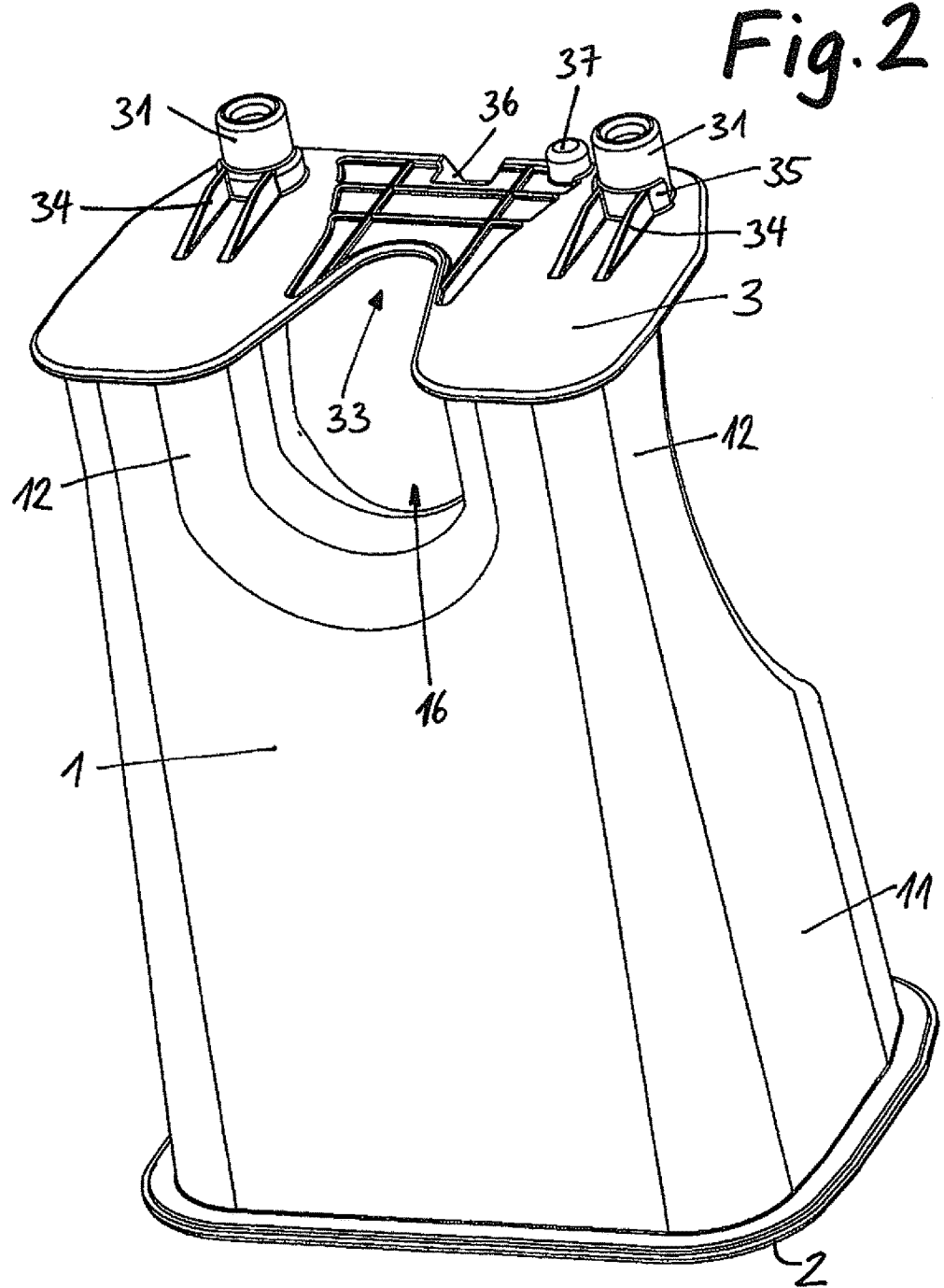
Figure 3:
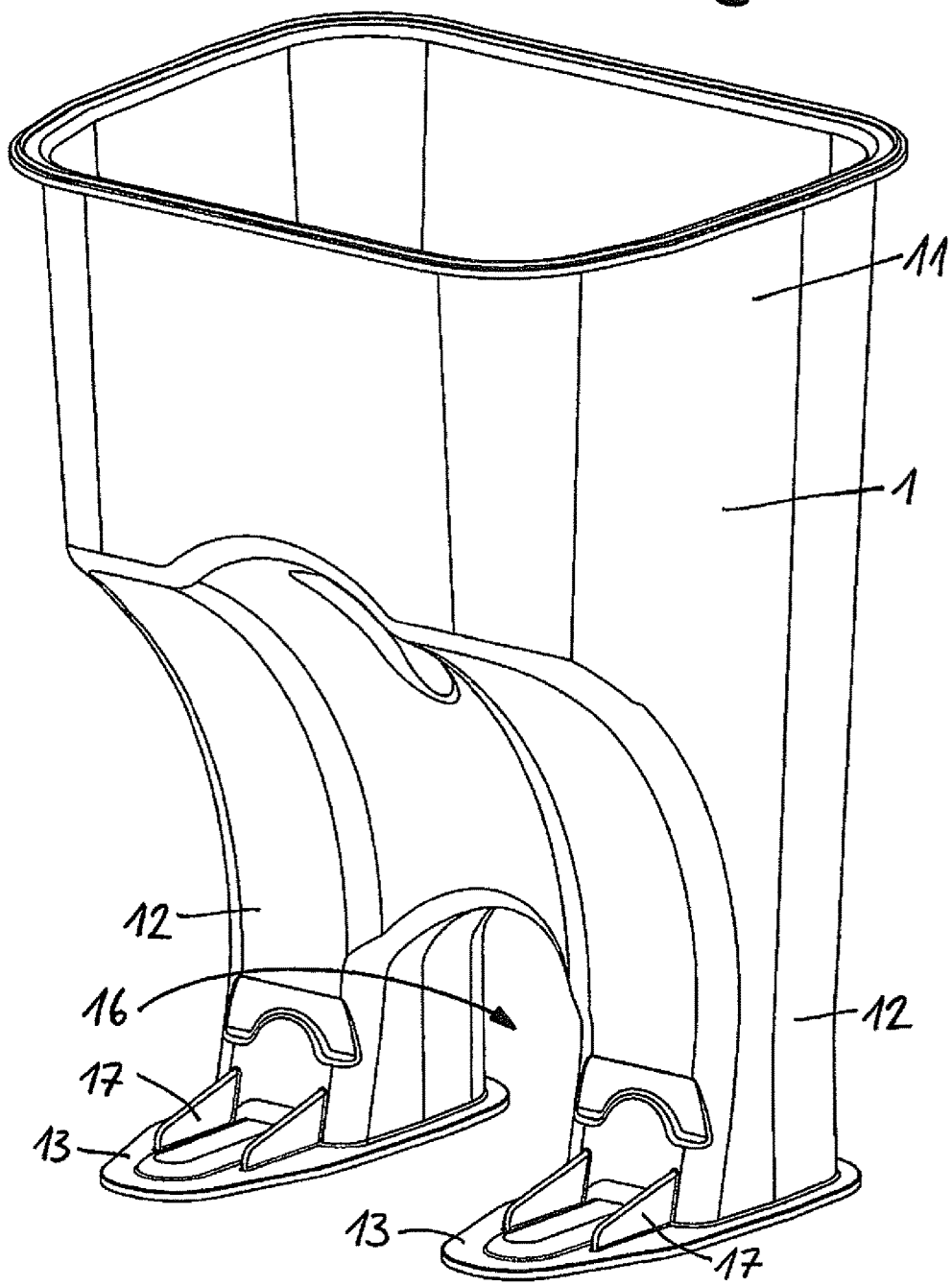
Figure 4:
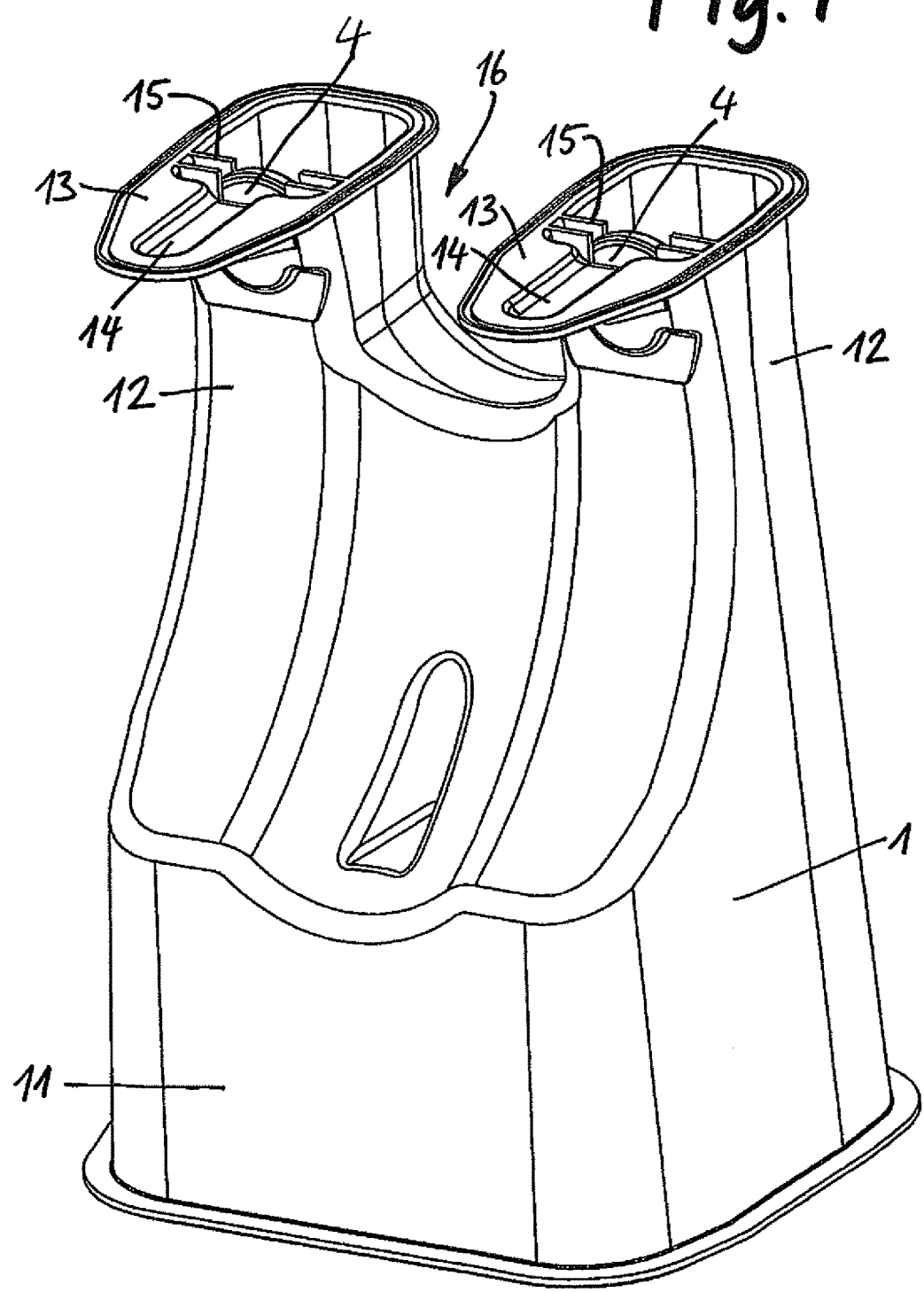

In the following, the present invention will be described in greater detail with reference to the accompanying drawings, in which:

FIG. 1 shows a perspective view of the complete dialysis concentrate container according to the invention, FIG. 2 shows, also in a perspective view, the complete dialysis concentrate container in an upside-down position, FIG. 3 shows a perspective view of the container body without top and bottom lids, FIG. 4 shows a perspective view of the container body standing upside-down without top and bottom lids, FIG. 5 shows the top container lid in a perspective view, FIG. 6 shows the bottom container lid in a perspective view, and FIG. 7 shows the bottom lid with plugged-in filter discs.

According to FIGS. 1 and 2, showing the complete dialysis concentrate container according to the invention in two different views, the container consists of a container body 1, a top lid 2 and a bottom lid 3.

FIGS. 1 and 2 show the dialysis concentrate container in a view onto its back side, i.e. the side facing the dialysis machine in use.

The container body 1 has an approximately rectangular cross-section in its upper region 11 and transitions into two laterally spaced legs 12 formed as hollow posts in its lower region.

The two legs 12 extend in the front region of the container body 1, which is shown in the illustrations according to FIGS. 1 and 2 in a view onto the rear of the dialysis concentrate container. From the illustrations, it can be seen that the container body 1 has a concave and arched narrowing taper from the lower end of its upper region 11 towards the front where it transitions into the two legs 12.

The arched tapering of the lower region of the container body 1 towards the front legs 12 provides the necessary space for the coupling mechanism of the dialysis machine when the dialysis concentrate container is coupled to the dialysis machine, so that the coupled container can rest close to the dialysis machine with its upper region.

The container body 1 is open at its upper end so that the dialysis concentrate can be easily filled in. This upper container opening is then closed with a lid 2, which is ultrasonically welded to the upper edge of the container body 1 or connected thereto in some other suitable way.

As can be seen from FIG. 1, the top lid 2 has a venting hole 21. As seen from the perspective view from the bottom according to FIG. 6, a film valve 22 with a film that closes the venting hole 21 and tears open, when a certain negative pressure occurs, is provided on the underside of the lid 2. The film has been omitted in the drawing to make the associated structure on the lid visible more clearly. The venting hole 21 and the associated film valve 22 facilitate the discharge of any residuals after use of the dialysis concentrate container, so that all treatment fluid can drain out of the container reliably without leaving behind any residual quantity.

At the lower end of the container body 1, horizontal plate elements 13 are formed on the opening edges of the legs 12 shaped as hollow posts, the plate elements protruding backwards, i.e., towards the dialysis machine, in the operating position. Together with the bottom lid 3 that has a complementary configuration, but forms a continuous plate (shown separately in FIG. 6), they form a connecting portion for connecting the dialysis concentrate container to the dialysis machine. The plate elements 13 could also be joined to form a continuous plate.

From the upside-down illustration of the container body 1 according to FIG. 4, it can be seen how the plate elements 13 are structured. The open mouths of the legs 12 are visible, each followed by a flat channel 14 formed into the respective plate element 13.

The bottom lid 3, shown in a perspective plan view in FIG. 6, is formed as a continuous plate and abuts against the lower sides of the plate elements 13 with its upper side, so that it delimits the channels 14 together with them. Two laterally spaced, downwardly protruding pipe sockets 31 are formed onto the bottom lid 3, which are respectively connected to one of the channels 14 when the bottom lid 3 is connected to the plate elements 13.

The bottom lid 3 can also be joined to the plate elements 13 of the container body 1 by ultrasonic welding, or in some other suitable way.

FIG. 4 shows the container body without top and bottom lids in an upside-down position. Webs 15 that extends into the interior of the hollow legs 12 can be seen here on the mouths of the lower ends of the legs 12 of the container body 1 (located at the top in this illustration), the webs serving to hold a circular filter disc in each case. FIG. 6 shows corresponding web formations 32 on the top side of the lid 3 which have a configuration complementary to the webs 15 in the legs 12 of the container body and which also serve to hold the filter discs 4. In FIG. 7, the lid is shown in the same way as in FIG. 6, but here, the filter discs 4 are inserted into the web formations 32 for illustration. The filter discs 4 held in this way separate the interior of the legs 12 of the container body 1 from the channels 14, and the filter discs 4 are configured in such a way that liquid, but no solid dialysis concentrate, can pass through.

As can be seen from FIGS. 1 and 3, stiffening ribs 17 are provided on the body of the container 1, which connect the plate elements 13 to the legs 12. This stiffening prevents the container from tipping over slightly under the increased weight during operation when it is filled with treatment fluid and the connecting portion bends out.

As shown in FIG. 2, additional stiffening ribs 34 are arranged on the underside of the bottom lid 3 and connect the stop elements 35 formed onto the pipe socket 31 to the bottom surface of the lid. They serve the same purpose as the stiffening ribs 17.

A roof-shaped formation 36 on the bottom lid 3 forms a support point adapted to the connection block of the dialysis machine, which cooperates with two other locations on the lower parts of the bottom lid 3 to form a three-point support against the connection block.

During the coupling, a pin 37 on the underside of the bottom lid activates a sensor button on the connection block of the dialysis machine, so that it detects that a dialysis concentrate container has been coupled thereto.

In the manufacture of the dialysis concentrate container according to the invention, the container body 1 as well as the upper lid 2 and the bottom lid 3 are each produced separately by injection molding. Then, the filter discs 4 are inserted into the lower openings of the legs 12 of the container body 1 and then the bottom lid 3 is placed thereon and, for example, ultrasonically welded to the plate elements 13 at the lower ends of legs 12.

The raw container formed in this way from the container body 1 and the associated bottom lid 3 with inserted filter discs 4 can then be filled with dialysis concentrate, such as bicarbonate, and finally closed by attaching the upper lid 2.

The dialysis concentrate container can be connected to a dialysis machine by means of the connecting portion formed from the plate elements 13 and the lid 3, wherein the pipe sockets 31 are inserted into corresponding connection openings of a connection block of the dialysis machine; the plate-shaped connecting portion of the dialysis concentrate container formed from the plate elements 13 and the lid 3 is clamped into a clamping mechanism of the connection block of the dialysis machine in its central region between the two pipe sockets 31, in order to secure the connection of the dialysis concentrate container with the connection block of the dialysis machine.

Together with an incision 33 in the bottom lid 3 that extends backwards from the leading edge of the bottom lid 3 between the lower ends of the two legs 12 of the container body when the bottom lid is attached to the container body 1, the free space 16 formed in the lowest region of the container body 1 between the two laterally spaced legs 12 forms a reach-through opening. This allows the user to reach through with their fingers from the front side of the dialysis machine without problems, in order to close and open the clamping device of the connection block of the dialysis machine for coupling the dialysis concentrate container to the dialysis machine, or for removing the dialysis concentrate container from the dialysis machine.

In operation, one of the two pipe sockets 31 serves as a liquid inlet and the other one of these pipe sockets serves as a liquid outlet, and the two legs 12 of the container body 1 respectively form an inlet channel and a drain channel, so that treatment fluid can flow through the dialysis concentrate container by means of the connections with the dialysis machine, and thereby the granular dialysis concentrate in the container can be dissolved and washed out.

At the end of the treatment, when the treatment fluid is removed from the dialysis machine, the resulting negative pressure inside the container causes the film valve 22 on the inner side of the top lid 2 to tear open, and thus brings about the venting of the interior of the container so that the treatment fluid can drain off completely. This process is supported by the force of gravity, as the entire inner volume of the container is located above the fluid connections of the dialysis machine.

The invention claimed is:

1. A dialysis concentrate container for single-use, comprising a container portion which can be filled with dialysis concentrate and a connecting portion connected thereto for connecting the dialysis concentrate container to a dialysis machine, the connecting portion having laterally spaced fluid connection elements for connecting to a fluid outlet and a fluid inlet of the dialysis machine,
   wherein the container portion is configured as a rigid box, wherein the connecting portion is further arranged at a lower end of the container portion, and wherein the connecting portion is formed by a plate body which can be clamped into a connecting block of the dialysis machine, the fluid connection elements being formed on a lower side of the plate body, wherein one of the fluid connection elements is connected with a fluid inlet of the container portion and the other one is connected with a fluid outlet thereof, and wherein the container portion has an upper region forming a box and lower region having transitions into two laterally spaced legs which are connected to the connecting portion and are formed as hollow posts, one forming the fluid inlet and the other one forming the fluid outlet of the container portion, respectively.

2. The dialysis concentrate container according to claim 1, wherein the container portion consists of a container body that is open at its top, and an upper lid which can be connected thereto and closes it at the top.

3. The dialysis concentrate container according to claim 1, wherein the container body has horizontal plate elements formed onto the open lower ends of the legs, the plate elements forming the connecting portion together with a bottom lid which can be connected thereto, and wherein the connection elements are formed onto the bottom lid, and wherein channels are formed into the plate elements and/or in the bottom lid, the channels respectively connecting one of the connection elements to a lower end of one of the two hollow legs.

4. The dialysis concentrate container according to claim 1, wherein the legs are formed in a front region of the container portion facing away from the dialysis machine in a position of use, wherein the container body is tapering towards the front, below its upper region and transitions into the legs, and wherein the connecting portion extends in a backward direction from the lower ends of the legs and towards the dialysis machine.

5. The dialysis concentrate container according to claim 4, wherein a free space formed between the two laterally spaced legs of the container body that are formed as hollow posts, and an incision in the connecting portion formed in the region between the lower ends of these two legs, together form a reach-through opening which enables the user to close or to open a clamping device of the dialysis machine in order to clamp or release the connecting portion of the dialysis concentrate container.

6. The dialysis concentrate container according to claim 4, wherein the container body portion is tapering towards a front thereof below its upper region in the form of a concave arch transitioning into the legs.

7. The dialysis concentrate container according to claim 1, wherein a filter disc is inserted between each of the fluid inlet and the fluid outlet of the container portion and the respective fluid connection element each said filter disc allowing liquid to pass through, but retaining solid dialysis concentrate.

8. The dialysis concentrate container according to claim 7, wherein the filter discs are each inserted into a lower end of each leg of the container portion.

9. The dialysis concentrate container according to claim 7, wherein the filter discs are arranged between the respective interior of the hollow legs and the channel connected thereto, and wherein the filter discs are retained by complementary web formations in the hollow legs and on the bottom lid.

10. The dialysis concentrate container according to claim 2, wherein a venting opening is provided in the upper lid and covered by a film valve on the inside of the lid, wherein the film valve is adjusted to tear open when a certain negative pressure occurs in the interior of the container, in order to allow air to enter through the venting opening.

11. The dialysis concentrate container according to claim 1, wherein the container portion composed of a container body and an upper lid, and the connecting portion formed by a bottom lid are formed as plastic parts made by injection molding.

* * * * *